(12) United States Patent
Mukherjee et al.

(10) Patent No.: US 11,001,744 B2
(45) Date of Patent: May 11, 2021

(54) FOAM-FORMING COMPOSITION FOR STEAM ASSISTED OIL RECOVERY

(71) Applicant: Dow Global Technologies LLC, Midland, MI (US)

(72) Inventors: Biplab Mukherjee, Pearland, TX (US); Matthew E. Crosley, Lake Jackson, TX (US); Yuko Kida, Houston, TX (US); Zhi Shi, Richmond, TX (US); Harpreet Singh, Pearland, TX (US); Zhe Zhou, Lake Jackson, TX (US)

(73) Assignee: Dow Global Technologies LLC, Midland, MI (US)

(*) Notice: Subject to any disclaimer, the term of this patent is extended or adjusted under 35 U.S.C. 154(b) by 117 days.

(21) Appl. No.: 16/312,305

(22) PCT Filed: Jul. 10, 2017

(86) PCT No.: PCT/US2017/041391
§ 371 (c)(1),
(2) Date: Dec. 21, 2018

(87) PCT Pub. No.: WO2018/013488
PCT Pub. Date: Jan. 18, 2018

(65) Prior Publication Data
US 2019/0233717 A1 Aug. 1, 2019

Related U.S. Application Data

(60) Provisional application No. 62/361,225, filed on Jul. 12, 2016.

(51) Int. Cl.
*C09K 8/584* (2006.01)
*C09K 8/592* (2006.01)
(Continued)

(52) U.S. Cl.
CPC .............. *C09K 8/584* (2013.01); *C09K 8/592* (2013.01); *C09K 8/594* (2013.01); *C07C 309/24* (2013.01)

(58) Field of Classification Search
None
See application file for complete search history.

(56) References Cited

U.S. PATENT DOCUMENTS

| 3,174,542 A | 3/1965 | Reisberg |
| 3,508,612 A | 4/1970 | Reisberg et al. |
(Continued)

FOREIGN PATENT DOCUMENTS

| WO | 1997010320 | 3/1997 |
| WO | 2001008793 | 2/2001 |
(Continued)

OTHER PUBLICATIONS

Cheng, Qing, "Assessing and Improving Steam-Assisted Gravity Drainage Reservoir Heterogeneities, Hydraulic Fractures, and Mobility Control Foams," Dissertation—Department of Energy Resources Engineering and the Committee on Graduate Studies of Stanford University, 2009, p. 1-197.
(Continued)

*Primary Examiner* — John J Figueroa

(57) ABSTRACT

The present invention includes a foam-forming composition for use in enhanced heavy oil recovery, and a method of using said foam-forming composition for recovering heavy oil and/or bitumen. The foam-forming composition of the present invention comprises a mixture of (di)alkyl diphenyloxide (di)sulfonate compounds and the process of heavy oil recovery is performed at elevated temperatures using steam.

8 Claims, 1 Drawing Sheet

(51) Int. Cl.
*C09K 8/594* (2006.01)
*C07C 309/24* (2006.01)

(56) References Cited

U.S. PATENT DOCUMENTS

| | | | |
|---|---|---|---|
| 3,675,716 A | 7/1972 | Farmer, III et al. | |
| 3,799,264 A | 3/1974 | Cardenas et al. | |
| 3,945,437 A | 3/1976 | Chiu et al. | |
| 4,013,569 A | 3/1977 | Chiu et al. | |
| 4,344,485 A | 8/1982 | Butler | |
| 4,380,266 A | 4/1983 | Wellington | |
| 4,393,937 A | 7/1983 | Dilgren et al. | |
| 4,540,049 A | 9/1985 | Hawkins et al. | |
| 4,607,700 A * | 8/1986 | Duerksen | C09K 8/592 166/303 |
| 4,702,317 A * | 10/1987 | Shen | E21B 43/24 166/272.1 |
| 4,739,831 A | 4/1988 | Settlemeyer et al. | |
| 4,860,828 A | 8/1989 | Oswald et al. | |
| 5,005,644 A | 4/1991 | Wall et al. | |
| 5,052,478 A | 10/1991 | Nakajima et al. | |
| 5,203,411 A | 4/1993 | Dawe et al. | |
| 5,215,146 A | 6/1993 | Sanchez | |
| 5,502,538 A | 3/1996 | Ogasawara | |
| 6,743,764 B1 | 6/2004 | Wallick et al. | |
| 2009/0078414 A1 | 3/2009 | Horvath Szabo et al. | |
| 2009/0218099 A1 | 9/2009 | Hart et al. | |
| 2012/0125620 A1 * | 5/2012 | Nguyen | E21B 43/12 166/309 |
| 2012/0220502 A1 | 8/2012 | Jurgenson et al. | |
| 2014/0216739 A1 * | 8/2014 | Brown | C09K 8/592 166/272.3 |
| 2015/0198027 A1 * | 7/2015 | Wickramathilaka | C09K 8/594 166/272.4 |
| 2017/0226836 A1 * | 8/2017 | Sanders | E21B 43/2408 |

FOREIGN PATENT DOCUMENTS

| | | |
|---|---|---|
| WO | 2014099466 | 6/2014 |
| WO | 2014160563 | 10/2014 |

OTHER PUBLICATIONS

PCT/US2015/021253, International Search Report and Written Opinion dated Mar. 18, 2015.

* cited by examiner

FOAM-FORMING COMPOSITION FOR STEAM ASSISTED OIL RECOVERY

FIELD OF THE INVENTION

This invention relates to a foam-forming composition and method of use thereof for foam steam assisted oil recovery process. Specifically, the foam-forming composition comprises primarily a dialkyl diphenyloxide disulfonate.

BACKGROUND OF THE INVENTION

The present invention relates to a composition and method for enhancing the recovery of crude oil and/or bitumen.

A common way of categorizing petroleum deposits is by density. Light oil, also known as "conventional oil", has an API gravity of greater than 22° and a viscosity less than 100 centipoise (cP). Heavy oil, by contrast, is an asphaltic, dense (low API gravity), and viscous hydrocarbon that is chemically characterized by its content of asphaltenes. Although definitions vary, the upper limit for heavy oils is usually an API gravity of 22° and a viscosity of more than 100 cP. Extra-heavy crude oil or bitumen has an API gravity of less than 10°.

In the recovery of conventional oil from reservoirs, the use of primary production techniques (i.e., the use of only the initial reservoir pressure to recover the crude oil) followed by the secondary recovery technique of waterflooding, recovers only a portion of the original oil present in the formation. Moreover, the use of certain enhanced oil recovery (EOR) techniques is also known in the art. These enhanced oil recovery techniques involve injection of any suitably tailored composition of fluids for example, water with tailored salinity, re-injection of hydrocarbon gases produced from the formation, in cases of heavy oil thermal methods can be used by increasing the enthalpy of injected fluid e.g., utilizing steam, and injection of chemicals like surfactants and polymers to enhance performance of any of these recovery techniques.

Usually heavy oil from an oil-bearing formation and/or bitumen from oil sands are produced by reducing the viscosity of the oil enough to make it flow. Viscosity reduction can be achieved by applying heat, often in the form of steam, and/or adding solvents to partially dilute the oil. There are several different EOR steam utilization techniques for extracting heavy oil and/or bitumen, for example: cyclic steam simulation (CSS), steam flood, steam assisted gravity drainage (SAGD), foam-assisted SAGD, and vapor extraction process (VAPEX). These methods employ injecting high temperature steam in the formation to reduce the oil viscosity followed by driving of the mobilized oil to the producer well either using a negative pressure, for example CSS, or positive pressure, for example steam flood.

In CSS, the same well acts as the injector and the producer and is also known as a huff and puff method. Steam is injected into a well at a temperature of 300-340° C. for a period of weeks to months. The well is allowed to sit for days to weeks to allow heat to soak into the formation, and, later, the hot oil is pumped out of the well for weeks or months. Once the production rate falls off, the well is put through another cycle of steam injection, soak and production. This process is repeated until the cost of injecting steam becomes higher than the money made from producing oil. Recovery factors are around 20 to 25%, but the cost to inject steam is high.

In steam flood, also known as steam drive, steam is injected into the formation through one vertical well; the heat of the steam helps lower the viscosity of the oil, and forces the mobilized oil to flow towards vertical producer wells located at certain distance from the producer. Although a promising technology, in steam floods after the initial injection breakthrough, the probability of steam bypassing the oil increases. With time, the active steam zone in the reservoir tends to bypass, or channel, the oil-bearing regions and limits the total amount of the formation that is effectively swept by the steam.

SAGD uses at least two horizontal wells—one at the bottom of the formation and another about 5 meters above it. Steam is injected into the upper well, the heat reduces the viscosity of the heavy oil, which allows it to drain by gravity into the lower well, where it is pumped to the surface. SAGD is cheaper than CSS, allows very high oil production rates, and recovers up to 60% of the oil in place.

VAPEX is similar to SAGD, but instead of steam, hydrocarbon solvents are injected into an upper well to dilute heavy oil which enables the diluted heavy oil to flow into a lower well.

Surfactants have been proposed as a means for generating foam in reservoir formations to reduce channeling. See, for example, U.S. Pat. Nos. 4,380,266; 4,540,049; 4,739,831; 4,860,828; 5,052,478; 5,005,644; 5,502,538; US Patent Application Nos. 2009/0078414, 2009/0218099, and 2014/0216739; WO 2014/160563, WO 2014/099466; and PCT/US 15/021253. The purpose of this foam is to block channeling and divert the flow of the steam into that portion of the formation containing high oil saturation.

Aqueous anionic surfactant systems are known to be particularly efficient as foaming agents. Such an anionic surfactant system is a substantially homogeneous aqueous liquid composition that may comprise a solution, a microemulsion, or a micellar dispersion of anionic surfactant molecules and/or micelles. The water-solubilities and oil-solubilities of the surfactants in such a system are such that those materials tend to remain along an oil/water interface, rather than being completely dissolved or dispersed within either the water-phase or oil-phase of the system. The anionic surfactants comprise surface active salts or soaps of organic acids.

In a process for displacing oil, the surfactants in an aqueous anionic surfactant system can be pre-formed or formed within permeable material such as a subterranean reservoir. U.S. Pat. No. 3,174,542 describes oil displacing processes in which acidic materials are injected ahead of basic materials so that surfactant systems are formed in situ.

Although aqueous anionic surfactant systems are generally efficient oil-displacing fluids, they have relatively low tolerances to multivalent cations. Such cations are commonly encountered in waters or brines in subterranean reservoirs that contain solutions of calcium or magnesium salts, or the like. The multivalent cations tend to react with the anionic surfactants or the components of anionic surfactants or the components of anionic surfactant systems to form precipitates, to cause phase separations, or the like.

Multivalent cation tolerance problems typical of aqueous anionic surfactant systems are discussed in patents such as U.S. Pat. Nos. 3,508,612 and 3,675,716. Those patents suggested improving the multivalent cation tolerance by dissolving co-surfactant such as alkoxy-alcohol sulfates in the systems. U.S. Pat. No. 3,799,264 suggests using surfactant systems that contain sulfated aliphatic anionic surfactants, nonionic surfactants, and a water-soluble guanidine salt, in order to provide an improved tolerance to multivalent cations.

It is taught that improved aqueous anionic surfactant systems can be employed in displacing oil within remotely located permeable subterranean reservoirs in U.S. Pat. Nos. 3,945,437; 4,013,569; and 4,393,937. For example, it is taught in U.S. Pat. No. 4,393,937 that a steam foam drive process can be employed in displacing oil within a subterranean reservoir.

In view of the fact that high foaming, thermally stable, brine and divalent ion tolerant surfactants are desirable for use in displacing oil from subterranean reservoirs, it would be highly desirable to provide such surfactants.

There is a continued need for an enhanced oil recovery technique that can be performed at elevated temperatures typically used in steam applications to further increase or maintain the recovery yields by chemical means, but not reduce the energy spent on recovery of heavy oils.

SUMMARY OF THE INVENTION

The present invention is a foam-forming composition and method of use in a steam assisted oil recovery process wherein the composition comprises an anionic surfactant wherein the anionic surfactant is a mixture of (di)alkyl diphenyloxide (di)sulfonate compounds having the formula:

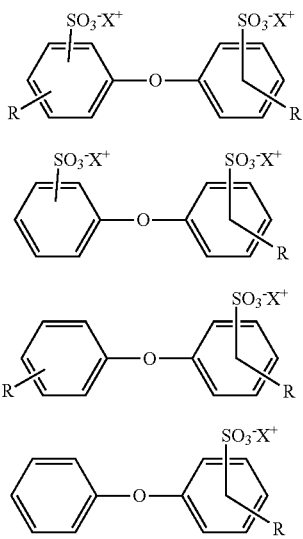

where R is a $C_3$ to $C_{24}$ alkyl group, preferably a $C_{16}$ group and X is H, an alkali metal, divalent metal e.g., calcium, magnesium, and the like, alkaline earth metal, or ammonium, wherein the aqueous mixture of (di)alkyl diphenyloxide (di)sulfonate compounds has a pH equal to or greater than 7 and contains I, the dialkyl diphenyloxide disulfate (DADS), in an amount equal to or greater than 50 weight percent with the remaining 50 weight percent or less comprising one or more of II, the monoalkyl diphenyloxide disulfate (MADS), III, the dialkyl diphenyloxide monosulfate (DAMS), and/or IV, the monoalkyl diphenyloxide monosulfate (MAMS), weight percent based on the combined weight of mixture of (di)alkyl diphenyloxide (di)sulfonate compounds.

Another embodiment of the present invention is a method for recovering oil from a reservoir formation that is penetrated by at least one injection well and one production well, comprising: (a) selecting a foam-forming composition comprising an aqueous mixture comprising two or more (di)alkyl diphenyloxide (di)sulfonate disclosed herein above, (b) injecting the foam-forming composition with steam into the injection well and forming a stable foam in the reservoir; (c) lowering a viscosity of oil in the reservoir formation; and (d) producing oil having the lowered viscosity from the reservoir formation.

In one embodiment of the present invention, in the foam-forming composition disclosed herein above R is a $C_{16}$ alkyl group and X is sodium.

In another embodiment of the present invention the foam-forming composition disclosed herein above further comprises one or more additive selected from a nonionic surfactant, an ionic surfactant, a corrosion inhibitor, a scale inhibitor, an antioxidant, a nonionic surfactant, an alcohol, another anionic surfactant, different from (i), a cationic surfactant, a foaming agent, and mixtures thereof.

In one embodiment of the method of the present invention described herein above, the injection well and the production well are the same well, preferably the method is cyclic steam stimulation (CSS).

In one embodiment of the method of the present invention described herein above, the injection well and the production well are not the same well, preferably the method is steam assisted gravity drainage (SAGD).

DETAILED DESCRIPTION OF THE INVENTION

Figure 1:
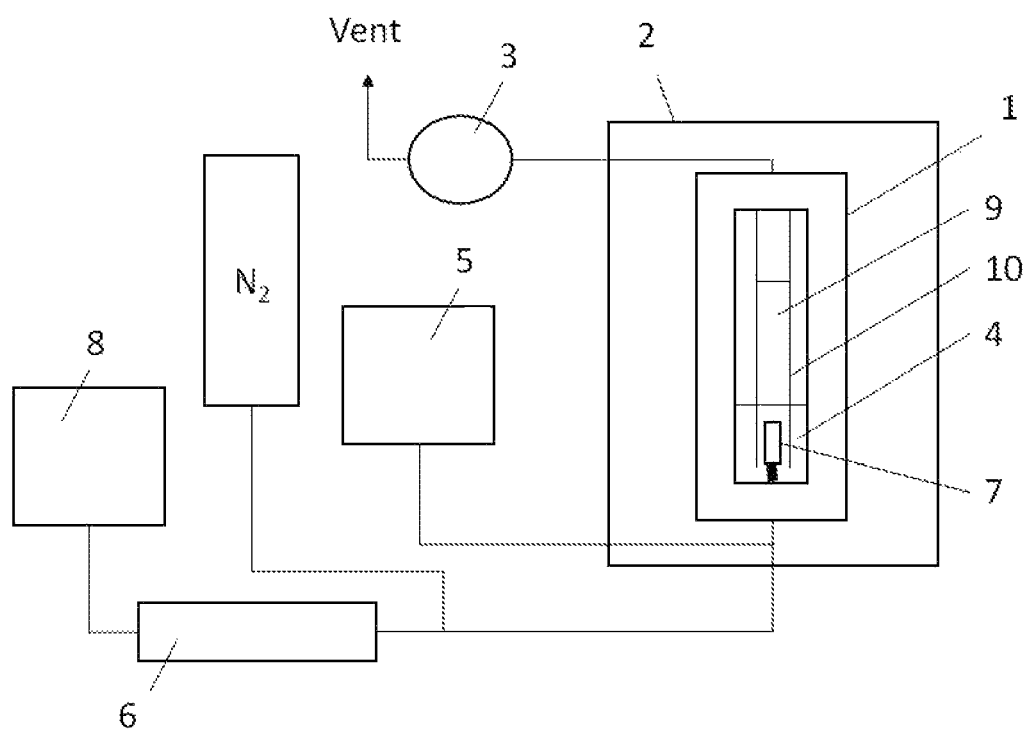
FIG. 1 is a schematic of the experimental apparatus used to determine foam stability.

Described herein are methods for removal of heavy oils from underground reservoirs. The term "heavier crudes" is any source or form of viscous oil. For example, a source of heavier crudes includes tar sand. Tar sand, also referred to as oil sand or bituminous sand, is a combination of clay, sand, water, and bitumen. The thermal recovery of heavier crudes is based on the viscosity decrease of fluids with increasing temperature. Once the viscosity is reduced, the mobilization of fluids by steam, hot water flooding, or gravity is possible. The reduced viscosity makes the drainage quicker and therefore directly contributes to the recovery rate.

In one aspect, the method comprises recovering oil from a reservoir formation that is penetrated by at least one injection well and one production well comprising the steps of injecting into the reservoir (i) a foam-forming composition which comprises, consists essentially of, or consists of a mixture of (di)alkyl diphenyloxide (di)sulfonate compounds and steam, (ii) lowering a viscosity of oil in the reservoir formation, and (iii) removing the oil from the reservoir.

In one embodiment of the method of the present invention the injection well and the production well are the same well.

In another embodiment of the method of the present invention the injection well and the production well are not the same well, but are two different wells.

Steam techniques known in the art for removing heavier crudes can be used herein, including, but not limited to CSS, steam flood, SAGD, FA-SAGD, and VAPEX. In general, steam is injected into the underground reservoir thereby heating the oil, reducing its viscosity making it more mobile, and recovering at least a fraction of reservoir hydrocarbons. After the initial injection steam breakthrough, the probability of steam bypassing the oil increases, which limits the total amount of the formation that is effectively swept by the steam. Next, surfactants, with or without a non-condensable gas (e.g., nitrogen), and steam are introduced into the injection well either periodically or continuously. The oil may be recovered in a production well separate from the injection well.

The SAGD process, invented by Butler in the early 80's (e.g., U.S. Pat. No. 4,344,485) has been the most popular thermal recovery process used to date in the production of heavy oil and bitumen. In the SAGD process, at least two horizontal wells are drilled, one over the other, and steam is injected into the upper well. The hot steam creates an expanding steam chamber, where the heat is transferred from the condensation of the steam mobilizes the oil, which then gravity drains around the edge of the steam chamber into the lower well along with any condensed water. The heat is transferred, by both conduction and convection, first to the condensate that flows along the edge of the steam chamber, and then the adjacent oil. As the oil is removed and more steam is injected, the boundary of the steam chamber expands upwards and sideways, and new oil is mobilized. The advantage of the SAGD process is its high oil production rate, recovering as much as 60-70% of the oil in place.

In one embodiment of the present invention is a method of producing oil by SAGD, said method comprising the steps of providing in an oil formation a horizontal injection well and a horizontal production well beneath said horizontal injection well, wherein said injection well and said production well are in fluid communication with each other; injecting steam and a foaming agent comprising an anionic surfactant, described herein below, into said injection well for a first period of time; collecting a production fluid from said production well.

The method of the present invention is not limited to SAGD and other such gravity drainage methods. The method of the present invention can be used in any known or invented steam-based enhanced oil production methods. Thus, the method can be used with toe to heel steam production methods, steam flooding techniques using vertical wells, cyclic steam stimulation (CSS), steam and gas push (SAGP), steam flooding, and the like, as well as in any of the hybrid methodologies, such as expanding solvent-SAGD (ES-SAGD), solvent aided process (SAP), and the like. Furthermore, the method can be used after any of the existing EOR methods.

The choice of water for use in the method of the present invention is typically the produced water, e.g., from the reservoir, but the source may be different, based upon the requirements of the reservoir to be treated, economics, and compatibility of the composition upon dilution, for example fresh water, aquifer water, or reservoir brine produced from the well. This invention will find particular applicability with brines having a total dissolved solids (TDS) content of from 0 up to 18 weight percent, preferably with 0 up to 15, and more preferably 0 up to 12 weight percent.

In another embodiment of the present invention, gases can be co-injected with the steam and surfactant. Suitable gases include, but are not limited to air, oxygen, hydrogen, nitrogen, methane, carbon dioxide, carbon monoxide, hydrogen sulfide, propane, butane, natural gas, and flue gas. Gases may come in the form of a gas/liquid mixture; including natural gas liquids containing propane, butane, pentane, and hexane.

The foam-forming composition employed in the present invention comprises one or more anionic surfactant, preferably comprising a mixture of alkyl aryl-sulfonate compounds. Suitable alkyl aryl-sulfonate compounds are products based on mono- and di-alkylated diphenyl oxide mono- and di-sulfonates (mono- and di-alkylates herein after referred to as (di)alkylates and mono- and di-sulfonates herein after referred to as (di)sulfonates). Preferred (di)alkyl diphenyloxide (di)sulfonate compounds are described by one or more of the following formulas:

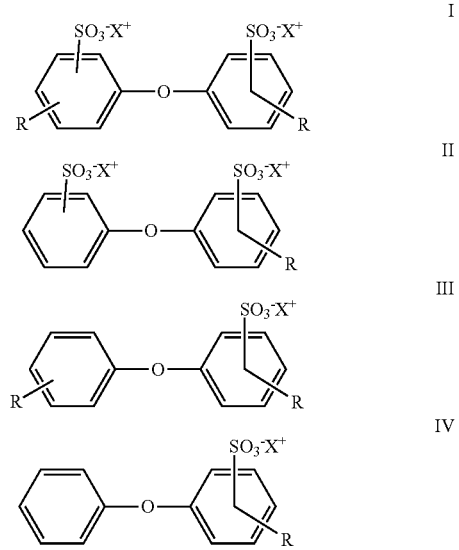

where R is a $C_3$ to $C_{24}$ alkyl group, preferably a $C_{16}$ group and

X is H, an alkali metal, alkaline earth metal, divalent metal, preferably calcium or magnesium, or ammonium.

Structure I represents a dialkyl diphenyloxide disulfonate (DADS), Structure II represents a monoalkyl diphenyloxide disulfonate (MADS), Structure III represents a dialkyl diphenyloxide monosulfate (DAMS); and Structure IV represents a monoalkyl diphenyloxide monosulfate (MAMS). Preferably the mixture of (di)alkyl diphenyloxide (di)sulfonate compounds contains DADS in an amount equal to or greater than 50 weight percent of DADS with the remaining 50 weight percent or less comprising one or more of MADS, DAMS, and/or MAMS, weight percent based on the combined weight of the mixture of (di)alkyl diphenyloxide (di)sulfonate compounds. More preferably the mixture of (di)alkyl diphenyloxide (di)sulfonate compounds contains DADS in an amount equal to or greater than 70 weight percent of DADS with the remaining 30 weight percent or less comprising one or more of MADS, DAMS, and/or MAMS, weight percent based on the combined weight of the mixture of (di)alkyl diphenyloxide (di)sulfonate compounds. Most preferably the mixture of (di)alkyl diphenyloxide (di)sulfonate compounds contains DADS in an amount equal to or greater than 85 weight percent of DADS with the remaining 15 weight percent or less comprising one or more of MADS, DAMS, and/or MAMS, weight percent based on the combined weight of the mixture of (di)alkyl diphenyloxide (di)sulfonate compounds.

In one embodiment, the mixture of (di)alkyl diphenyloxide (di)sulfonate compounds comprise MADS in an amount of 0.05 to 15 weight percent, DAMS in an amount of 0 to 10 weight percent, MAMS in an amount of 0 to 5 weight percent, and DADS in an amount of equal to or greater than 50 to 90 weight percent, wherein higher alkylates of mono- and di-sulfonates makes up the balance of the mixture.

In another embodiment, the mixture of (di)alkyl diphenyloxide (di)sulfonate compounds comprise MADS in an amount of 0.05 to 15 weight percent, DAMS in an amount of 0 to 7.5 weight percent, and MAMS in an amount of 0 to 2 weight percent, wherein DADS makes up the balance of the mixture with the proviso that it is present in an amount equal to or greater than 50 weight percent, weight percent based on the combined weight of the mixture of (di)alkyl diphenyloxide (di)sulfonate compounds.

Suitable (di)alkyl diphenyloxide (di)sulfonates of the present invention can be prepared by methods recognized in the art. For example, attention is directed towards U.S. Pat. No. 4,860,828 to Oswald et al. which is incorporated herein by reference.

The mixture of (di)alkyl diphenyloxide (di)sulfonate compounds may be added neat or preferably in solution, preferably an aqueous solution having a pH equal to or greater than 7, more preferably equal to or greater than 7.5, more preferably equal to or greater than 8, and more preferably equal to or greater than 8.5.

The (di)alkyl diphenyloxide (di)sulfonate compounds are added down hole and/or to the steam neat and/or diluted with water to form an aqueous solution and then added, such that the amount of the (di)alkyl diphenyloxide (di)sulfonate compounds in the steam present down-hole is from 0.0001 to 0.5 weight percent. Preferably, the amount of anionic surfactant in the down-hole water is equal to or greater than 0.0001 weight percent, more preferably equal to or greater than 0.001 weight percent, more preferably equal to or greater than 0.01 weight percent, more preferably equal to or greater than 0.05 weight percent, and even more preferably equal to or greater than 0.08 weight percent. Generally, the amount of the anionic surfactant is present in the water pumped down-hole in an amount equal to or less than 0.5 weight percent, preferably equal to or less than 0.3 weight percent, preferably equal to or less than 0.2 weight percent.

In some embodiments, foam-forming compositions of the present invention may include other additives. For example, the composition may further include one or more ionic surfactant, one or more nonionic surfactant, one or more alcohol, corrosion inhibitors, scale inhibitors, mixtures thereof, as well as other additives. In some embodiments, the total amount of the additives added to the compositions of the present disclosure is not greater than about 5 weight percent.

EXAMPLES

Preparation of (di)alkyl diphenyloxide (di)sulfonate compound.

Example 1 is a (di)alkyl diphenyloxide (di)sulfonate compound prepared in three steps: (a) alkylation of diphenyl oxide (DPO), (b) sulfonation of the alkylated product, and (c) neutralization using caustic solution.

Alkylation of DPO with olefin of specific chain length is done in the presence of aluminum chloride catalyst between 50° C. to 100° C. The Friedel-Crafts alkylation reaction generates isomeric mixture of mono-, di-, and higher polyalkylates from competitive reactions of olefins around the aromatic rings. Alkylation is carried out in presence of excess DPO to control relative amounts of monoalkylated DPO, dialkylated DPO, and higher alkylate DPOs.

Sodium hydroxide solution is then added to the reaction mixture to neutralize the aluminum chloride catalyst. This is followed by phase separation of the mixture by using a decanter. The crude product is then subjected to distillation to separate out the unreacted DPO, the unreacted olefins, and the final alkylated product. The alkylated end product is then distilled further to concentrate dialkylated and higher alkylated DPOs to greater than 50%.

The distilled alkylated product is then subjected to sulfonation by sulfur trioxide, which results in primarily the disulfonated products. The level of sulfonation is greater than 80%. While the sulfonation reaction is highly exothermic, the reaction is kept under isothermal conditions at or below room temp. Following sulfonation, water is added to remove any unreacted $SO_3$. The aqueous acid solution is then neutralized using caustic soda to get a final product with pH of equal to or greater than 7.

The resulting active product comprises 1 wt % monoalkyl diphenyloxide monosulfate (MAMS), 10 wt % monoalkyl diphenyloxide disulfate (MADS), 7. wt % dialkyl diphenyloxide monosulfate (DAMS), 75 wt % dialkyl diphenyloxide disulfate (DADS), and the rest being higher alkylates of mono- and di-sulfonates.

Foam Stability Test.

Figure 2:
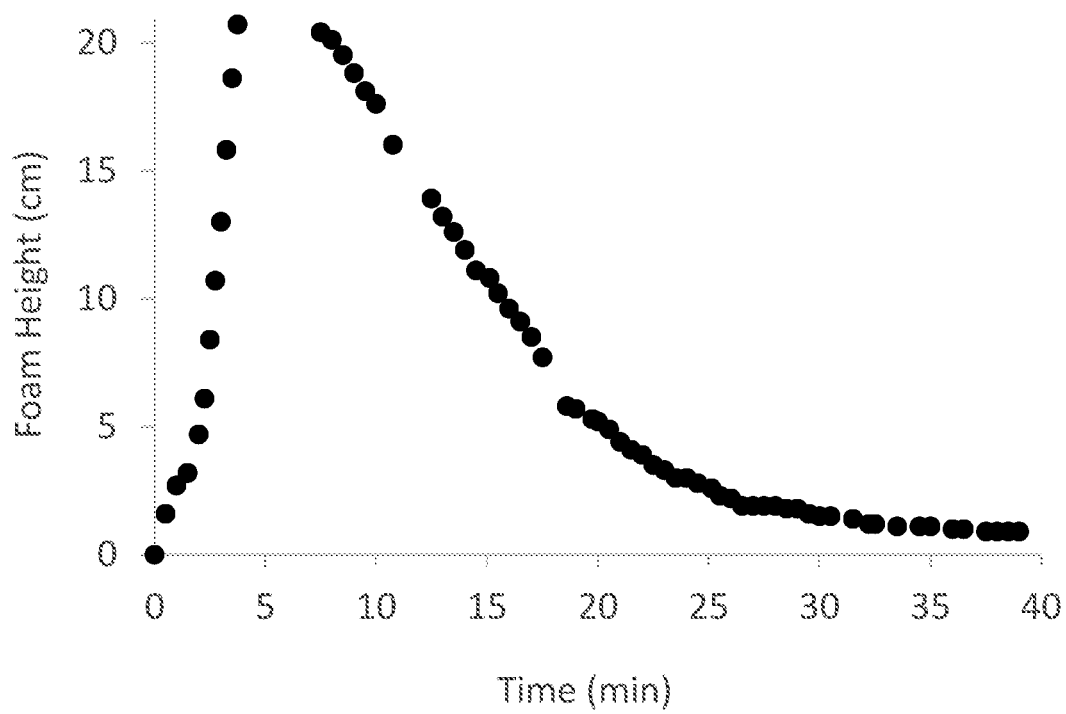
FIG. 2 is a plot showing foam height for Example 1 versus time.

The experimental set up is shown in FIG. 1. Initially, an empty JERGUSON19-T-32 series level gauge 1 is pressurized to 950 psi. The oven 2 is then heated up to 250° C. The pressure is maintained to 950 psi via the back pressure regulator (EQUILIBAR ULF-2) 3 at the exit line of the JERGUSON level gauge. 50 mL of a 0.5 wt % aqueous solution of Example 1 is prepared and its pH adjusted to 9.1 with a sodium hydroxide solution. 50 mL of this solution 4 is loaded into the JERGUSON level gauge via pump 2 5. The system is allowed to equilibrate to 250° C. for an hour. An accumulator (TOBUL 030AT30-1VA19) 6 is used to pump in nitrogen into this solution through a sparger having a 10 micron sintered metal filter element 7. Water is pumped into the accumulator at 2.7855 mL/min from pump 1 8 to achieve a flow rate of 180 sccm into the JERGUSON level. Pressure is maintained at 950 psi with the back pressure regulator. 0.2 mL/min of water is replenished through pump 2 5 since the system loses water at approximately this rate due to evaporation. As nitrogen flows into the chemical solution, foam 9 starts to rise up inside the glass cylinder 10 in the JERGUSON level gauge. The cylinder is open at top and bottom. Once the foam reaches the top of the level gauge, the nitrogen flow is stopped. The foam slowly decays. The foam height from the foam generation to collapse is recorded and is shown in FIG. 2.

What is claimed is:

1. A method for recovering oil from a reservoir formation that is penetrated by at least one injection well and one production well, comprising
   (a) selecting a foam-forming composition comprising
      (i) an aqueous mixture comprising two or more (di) alkyl diphenyloxide (di)sulfonate compounds having the formulas:

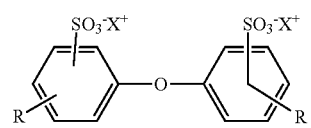

I

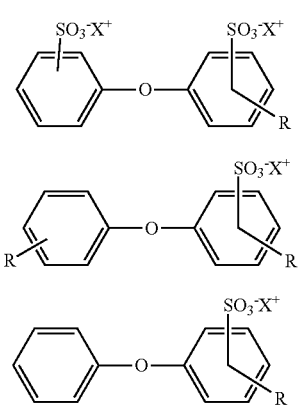

where R is a $C_3$ to $C_{24}$ alkyl group
and
X is H, an alkali metal, alkaline earth metal, a divalent metal, or ammonium, wherein the aqueous mixture of (di)alkyl diphenyloxide (di)sulfonate compounds has a pH equal to or greater than 7 and contains I, the dialkyl diphenyloxide disulfonate (DADS), in an amount equal to or greater than 50 weight percent with the remaining 50 weight percent or less comprising one or more of II, the monoalkyl diphenyloxide disulfonate (MADS), III, the dialkyl diphenyloxide monosulfonate (DAMS), and/or IV, the monoalkyl diphenyloxide monosulfonate (MAMS), weight percent based on the combined weight of the mixture of (di) alkyl diphenyloxide (di)sulfonate compounds;

(b) injecting the foam-forming composition with steam into the injection well and forming a stable foam in the reservoir;

(c) lowering a viscosity of oil in the reservoir formation; and (d) producing oil having the lowered viscosity from the reservoir formation.

2. The method of claim 1 wherein R is a $C_{16}$ alkyl group and X is sodium, calcium, or magnesium.

3. The method of claim 1, where the a foam-forming composition further comprises one or more additive selected from a corrosion inhibitor, a scale inhibitor, an antioxidant, a nonionic surfactant, another anionic surfactant, different from (i), a cationic surfactant, a foaming agent, and mixtures thereof.

4. The method of claim 1 where in the injection well and the production well are the same well.

5. The method of claim 4 is cyclic steam stimulation (CSS).

6. The method of claim 1 where in the injection well and the production well are not the same well.

7. The method of claim 6 is steam assisted gravity drainage (SAGD).

8. The method of claim 1 wherein the aqueous mixture of (di)alkyl diphenyloxide (di)sulfonate compounds has a pH equal to or greater than 7 and comprises at least 1 wt % monoalkyl diphenyloxide monosulfonate (MAMS), 10 wt % monoalkyl diphenyloxide disulfonate (MADS), 7 wt % dialkyl diphenyloxide monosulfonate (DAMS), 75 wt % dialkyl diphenyloxide disulfonate (DADS).

* * * * *